United States Patent [19]

Marquette

[11] Patent Number: 4,790,299

[45] Date of Patent: * Dec. 13, 1988

[54] KNEE STABILIZER

[76] Inventor: Stuart H. Marquette, 8604-A Via Mallorca Dr., La Jolla, Calif. 92037

[ * ] Notice: The portion of the term of this patent subsequent to Mar. 29, 2005 has been disclaimed.

[21] Appl. No.: 935,257

[22] Filed: Nov. 26, 1986

Related U.S. Application Data

[63] Continuation of Ser. No. 732,345, May 8, 1985, abandoned, which is a continuation-in-part of Ser. No. 579,728, Feb. 13, 1984, Pat. No. 4,733,656.

[51] Int. Cl.⁴ .............................. A61F 5/01; A61F 5/04
[52] U.S. Cl. .................................. 128/80 C; 128/80 F
[58] Field of Search ................ 128/80 R, 80 L, 80 F, 128/87 R, 165; 2/22, 24

[56] References Cited

U.S. PATENT DOCUMENTS

| | | | |
|---|---|---|---|
| 1,622,211 | 3/1927 | Sheehan | 128/80 C X |
| 3,387,305 | 6/1968 | Shafer | 2/22 |
| 3,575,166 | 4/1971 | Rosman et al. | 128/80 R |
| 3,581,741 | 6/1971 | Rosman et al. | 128/80 C |
| 4,041,940 | 8/1977 | Frankel et al. | 2/24 X |
| 4,275,716 | 6/1981 | Scott, Jr. | 128/80 C |
| 4,407,276 | 10/1983 | Bledsoe | 128/80 R X |
| 4,487,200 | 12/1984 | Feanny et al. | 128/80 F X |

FOREIGN PATENT DOCUMENTS 3123144  1/1983  Fed. Rep. of Germany ............ 2/24

Primary Examiner—Edgar S. Burr
Assistant Examiner—Tonya Lamb
Attorney, Agent, or Firm—Flehr, Hohbach, Test, Albritton & Herbert

[57] ABSTRACT

A knee brace having an anterior tibial shell and a posterior femural shell which are closely configured to the shape of the leg and are joined by a closed support band which is constructed to closely track knee flexion. The brace also has anteriorly extending tabs positioned between the patella and the femural epicondyles. The combination of shell, band and tabs provides anterior-posterior, medial-lateral and rotary stability.

2 Claims, 3 Drawing Sheets

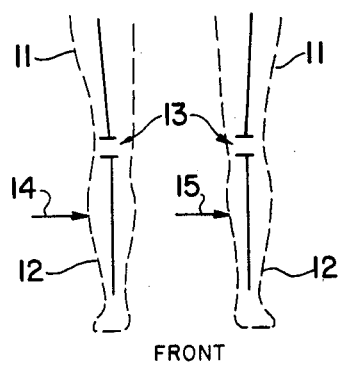
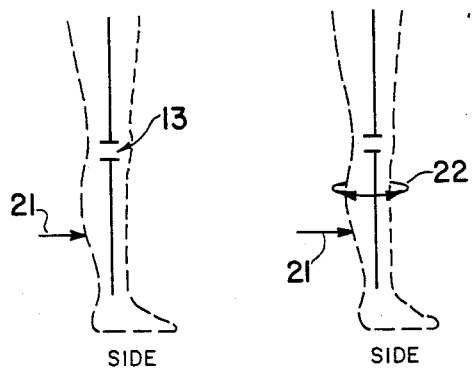
FIG. 1   FIG. 2A   FIG. 2B
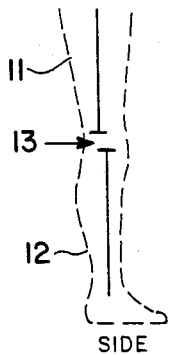
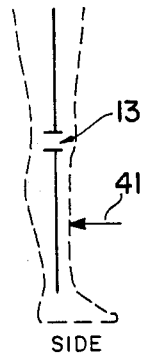
FIG. 3   FIG. 4
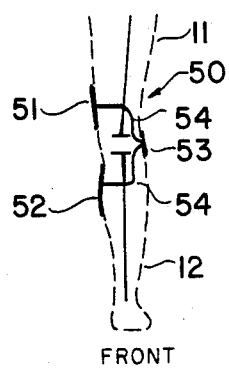
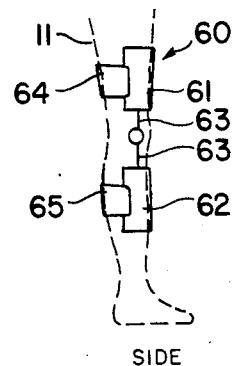
FIG. 5
PRIOR ART
FIG. 6
PRIOR ART

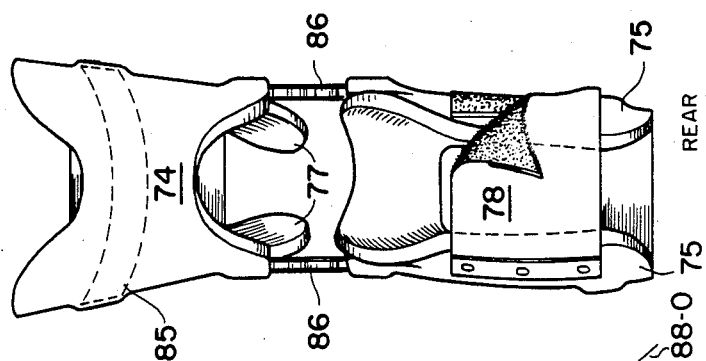
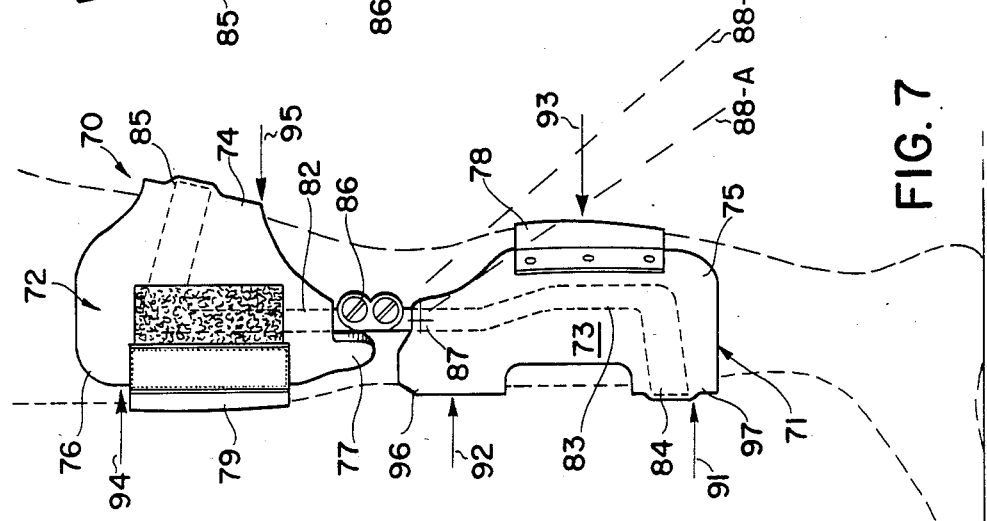
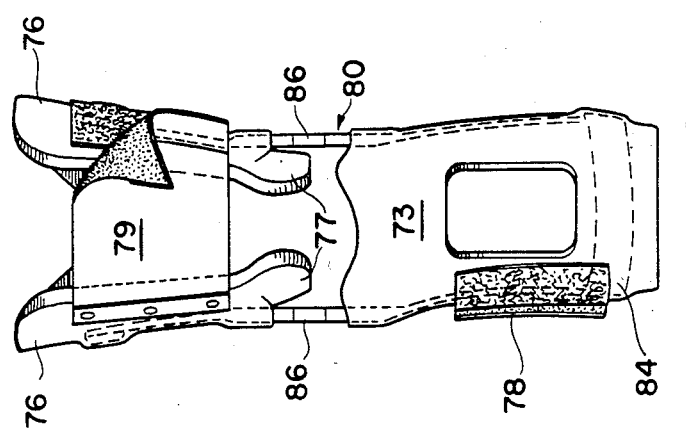

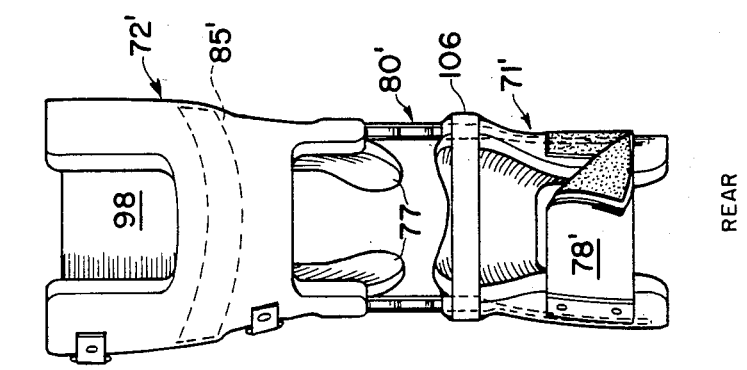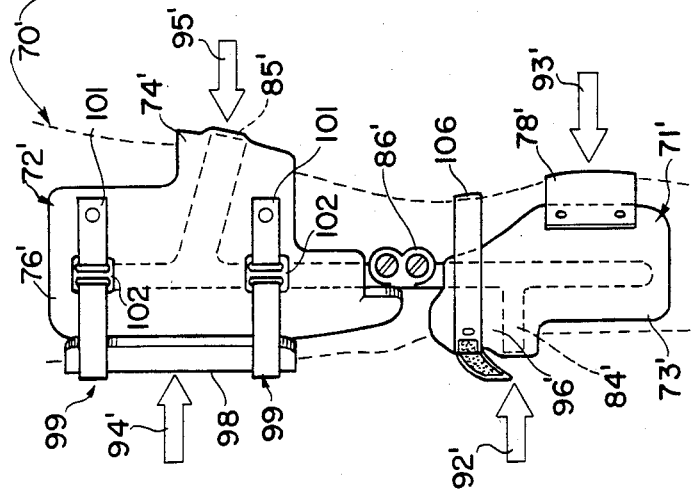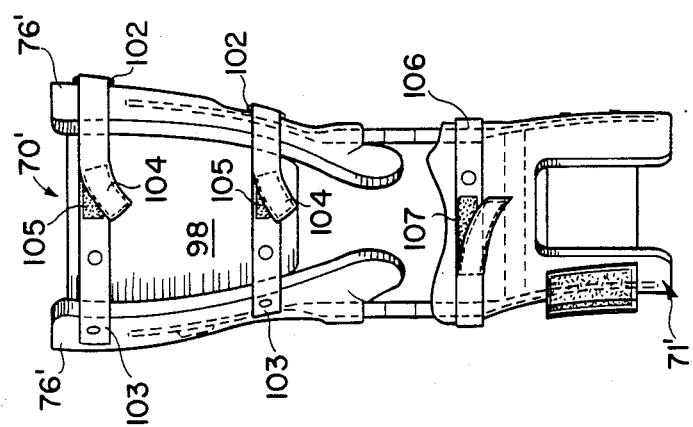

KNEE STABILIZER

This application is a continuation of co-pending application Ser. No. 752,345 filed May 8, 1985, now abandoned which is a continuation-in-part of my U.S. patent application, Ser. No. 579,728, filed Feb. 13, 1984, now U.S. Pat. No. 4,733,656.

BACKGROUND OF THE INVENTION

This invention relates to orthotics, to supports or stabilizers for joints and, in particular, to a knee brace which serves both preventive and remedial functions in protecting against medial-lateral, anterior-posterior and rotary instabilities.

The knee joint is perhaps the most susceptible to injury of the major articulated joints of the human body, despite the presence of five major ligaments and two menisci which serve to connect and stabilize the tibia and femur. These anatomical structures include the anterior and posterior cruciate ligaments, the medial and lateral collateral ligaments, the posterior capsule ligament and the medial and lateral menisci.

Anatomically, the knee is designed so that specific muscles or muscle groups, not ligaments, absorb the brunt of external or internal forces. That is, a muscle or group of muscles substitutes for each ligament in the knee to absorb force and restrict motion. As examples, the hamstrings substitute for the anterior cruciate ligament, the quadriceps for the posterior cruciate ligament, and the abductor and adductor groups for the medial and lateral collateral ligaments.

The articulation of the knee joint, and the ligaments, muscles and bones associated with the joint are described, for example, in Gray's Anatomy and in The Johns Hopkins Atlas of Human Functional Anatomy, 2d ed., 1980. These teachings are incorporated by reference.

When a muscle is unable to completely absorb an applied force, either because of inherent weakness or prior injury or simply because the force is too strong, the unabsorbed component of force is transmitted to one or more ligaments. If the transmitted component is sufficiently great, the ligament is strained or torn. Ligamental susceptibility to injury is also dependent upon the degree of flexion or extension. However, the inherent cooperation and relationship among the ligaments is such that when the knee is bent or flexed, some ligaments are relatively tight and tend to control displacement, but others are relatively loose. Between 20°-60° of flexion, the knee is very susceptible to displacement and to injury. This is unfortunate, because the knee is frequently in this position, particularly during the more active sports activities.

It is factors such as these which make the knee relatively weak compared to the other major articulated joints. Some, such as the ball and socket hip joint, are very secure. Others, such as the elbow and shoulder joints are complicated but nonetheless relatively secure. Despite its inherent weaknesses, the knee joint must both support the weight of the body and provide for movement, while holding the tibia and femur in position along their substantially planar unstable interface.

In considering external forces applied to the knee and the resulting ligament injuries, it is helpful to simplify the situation somewhat and consider the forces as having their major components applied primarily along a frontal plane through the knee, or along a sagittal plane through the knee, or as comprising a rotatory force. Frontal plane forces are medial-lateral forces which displace the femur and/or tibia in a side-to-side direction. Saggital plane forces are anterior-posterior forces which displace the femur and tibia in approximately a front-to-back motion, and includes drawering forces applied during flexion or extension. Rotatory forces are those which tend to induce relative rotational displacement of or between the femur and tibia, primarily against the stabilizing force provided by the anterior cruciate ligament.

FIGS. 1 through 3 illustrate examples of the above forces. In these schematic drawings, the femur, tibia and knee are respectively designated 11, 12 and 13. Referring specifically to FIG. 1, two of the more common knee ligament injuries result from medial and lateral forces. The medial collateral ligament and lateral collateral ligament are primary stabilizing influences against medial and lateral force, respectively. As a consequence, strains or tears of these ligaments tend to result, respectively, from medial forces, that is, inward or medially-directed forces 14 applied against the outside of the leg, or lateral forces 15, which are outward directed forces applied against the inside of the leg.

Perhaps the most frequent injury in sports, and certainly one of the most damaging injuries to the joints involves strains or tears of the anterior cruciate ligament. Referring to the side views shown in FIG. 2, the responsible force may involve an anterior tibial force alone, that is, a forward-directed force 21 applied to the back of the tibia. See FIG. 2A. The force may involve the combination of a rotational tibial force 22 which rotates the tibia relative to the femur (as by catching a shoe or cleats in turf) and an anterior tibial force 21. See FIG. 2B. In either case, injury to the anterior cruciate ligament results from excessive force which the substitutional muscles and the anterior cruciate ligament are unable to absorb and a resulting anterior tibial acceleration and displacement relative to the femur. See FIG. 3. The reason for the frequent occurrence of this injury is twofold, namely the frequency with which the knee and leg are subjected to large magnitude forces, and the susceptibility to injury in that typically the knee can withstand only about 380 pounds of force and 12.5 millimeters displacement or movement between the tibia and the femur without injury to the anterior cruciate ligament.

Referring to FIG. 4 and as shown by the arrow 41 therein, a posterior-directed force 41 is the opposite of anterior-directed force 21. The knee 13 is stabilized against posterior forces primarily by the posterior cruciate ligament. Unlike the anterior cruciate ligament, the posterior cruciate ligament is backed by the posterior capsule ligament, which is quite effective in stabilizing the knee against displacement. As a result, isolated posterior cruciate tears are rare. Usually injuries to other ligaments are also involved. In fact, it is not infrequent that the bone attachment itself tears rather than, or in addition to the posterior capsule ligament.

Displacement of the femur and tibia resulting from rotational forces such as 22, FIG. 2B, is another primary cause of injury to the anterior cruciate ligament. Of course, if there is existing damage or if the anterior cruciate ligament has inherent instability, the knee is more susceptible to displacement and the ligament is more susceptible to injury. The same is true of the other ligaments in that existing damage or instability increases their susceptibility to injury.

Concentrated efforts by the orthotics profession to develop knee stabilizers are thought to have been initiated in the 1960's as a result of publicized knee injuries suffered by professional athletes. It is believed basically two types of knee braces have dominated this field. Referring to the FIG. 5 front view, one such brace 50 uses a three-point suspension which is provided by two pads 51 and 52 situated above and below the knee (on either the medial or the lateral side of the leg) and a third pad 53 on the opposite side of the leg adjacent the knee. Rigid braces 54—54 correct the pads. Various straps can be used to enhance suspension and/or stabilization characteristics. Referring to the side view shown in FIG. 6, the second type 60 of conventional knee brace uses relatively rigid anterior femur and tibial shells 61 and 62 which are joined by hinged uprights 63—63 in the back or posterior side by elastic straps 64 and 65. These designs are more effective at protecting against medial-lateral forces than anterior-posterior forces. The reason is simple. The rigid shells/pads and connecting braces provide relatively inflexible pressure points which stabilize against lateral or medial forces.

In contrast, the relatively flexible front-to-rear stabilization systems provided by these braces permit relative movement of the tibia and femur along the sagittal plane.

In addition, because rotary stability is a function of both medial-lateral and anterior-posterior stability, the implementation of conventional knee brace designs tends to be less effective than desired in any derotation function. Furthermore, stabilization in all aspects is closely related to the effective suspension of the orthotic device on the knee and leg in a manner such that the device does not alter or shift its position on the leg as by planing. Many prior art devices experience planing and shifting which detract from their ability to provide medial-lateral stability, anterior-posterior stability and/or rotatory stability.

In addition to the difficulty of achieving adequate suspension stability using typical prior art knee braces, frequently such braces avoid the problems associated with flexion by restricting movement of the knee. Because of restrictions on movement and because of weight, the use of these braces to prevent injuries puts the athlete at such a competitive disadvantage that knee braces are not widely used for injury prevention. Rather, the primary use has been remedial, to compensate for and protect against existing injuries and weaknesses in already damaged and/or unstable knees. Perhaps the one exception to the use of prior art knee braces for remedial purposes rather than prevention is the class of braces which consist simply of a pair of upright bands on the sides of the leg. These are used to provide some means of protection against medial-lateral forces.

SUMMARY OF THE INVENTION

Accordingly, it is one object of the present invention to provide a new and improved knee brace suspension system which restricts planing and other movement of the knee brace relative to the leg and knee.

It is another object of the present invention to provide a new and improved knee brace which protects against displacement and injuries to the anterior cruciate ligament.

It is another object of the present invention to provide a new and improved knee brace which protects against displacement and medial-lateral, anterior-posterior and rotary instabilities.

In one embodiment, the knee stabilizer of the present invention contains a relatively rigid anterior tibial shell which substantially conforms to the outline of the leg proximate and distal to the knee; a relatively rigid posterior femural shell which substantially conforms to the outline of the thigh proximate the knee; and a pair of uprights extending one on the lateral side of the knee and one on the medial side of the knee for rigidly interconnecting the tibial and femural shells, and substantially tracking flexion of the knee. The tibial shell wraps partially around the posterior side of the leg, defining a posterior opening, and the femural shell wraps partially around the anterior side of the thigh, defining an anterior opening, and has a pair of suspension pads located on opposite sides of the patella between the patella and the femural epicondyles. A strap-type closure means is attached at each of the anterior femural opening and the posterior tibial opening for closing each opening to complete the suspension of the stabilizer. The combination of the partially open anterior tibial and posterior femural shells, the strap closure means and the uprights provides a combination of light weight, yet excellent anterior-posterior, medial-lateral and rotary stability.

In a preferred working embodiment, the uprights are part of a closed, rigid band support system including a femural section which is attached to the uprights on opposite sides of the femural shell and spans the posterior side of that shell, and a tibial section which is attached to the uprights on opposite sides of the tibial shell and spans the anterior side of that shell.

In a presently preferred, light-weight working version, my knee stabilizer is configured as a four-point pressure system. Here, the posterior border of the femural shell forms the first pressure point, and the femural shell anterior strap means supports an anterior plate for providing a second pressure point at about the height of the superior border of the femural shell, for cooperatively locking the femur to the femural shell and to the band system. The posterior strap of the tibial shell again forms the third pressure point. The tibial section of the band system is positioned at the closed superior border of the otherwise open anterior periphery of the tibial shell to form the fourth pressure point and, in cooperation with the third pressure point, provides a light-weight, two-point pressure system for locking of the tibia to the tibial shell and to the band system. The tibial shell preferably includes a circumferential superior strap which completes the enclosure of the tibial shell about the leg, or itself spans the circumference of the leg for, tibial inertial control, and for providing a stable suspension in conjunction with the suspension pads. The four-point pressure system provides medial-lateral, anterior-posterior, and rotary stability.

BRIEF DESCRIPTION OF THE DRAWINGS

FIG. 1 schematically illustrates the application of medial force and lateral force to the human leg.

FIGS. 2A and 2B schematically illustrate respectively application of an anterior tibial force and an external rotation anterior tibial force to the human leg;

FIG. 3 illustrates the resultant displacement of the tibia relative to the femur.

FIG. 4 schematically illustrates the application of a posterior tibial force to the human leg.

FIGS. 5 and 6 are, respectively, front and side schematic illustrations of two conventional knee braces.

FIGS. 7, 8 and 9 are, respectively, side, front and rear elevation views of the knee stabilizer of the present invention, including, in FIG. 7, illustration of the positioning of the knee stabilizer on the human leg.

FIGS. 10, 11 and 12 are, respectively, side, front and rear elevation views, in the manner of FIGS. 7, 8, 9, illustrating a light-weight, four-point pressure version of my knee stabilizer.

DETAILED DESCRIPTION

One preferred embodiment 70 of the knee stabilizer of the present invention is shown in FIGS. 7, 8 and 9. The knee stabilizer 70 comprises a tibial shell 71, a femural shell 72 and a closed band structure 80 which joins the two shells and includes a joint 86 on either side of the knee for substantially tracking flexion of the knee. The shells and band are carefully tailored and configured to conform to the shape and size of the individual leg and knee. The tibial shell 71 includes superior (upper) and inferior (lower) borders or sections 96 and 97 which span the anterior (front) side thereof and, particularly in applications requiring light weight, may be open at the posterior (rear) side. The phrase "anterior tibial shell" as used herein thus refers to tibial shell 71 having one or more sections which span the anterior side of the lower leg. Similarly, the femural shell 72 is closely configured to the size and shape of the thigh, and has a support section 74 which spans the posterior side of the thigh. Thus, as used here, the phrase "posterior femural shell" refers to a femural shell 72 which has a section 74 spanning the posterior side of the thigh. In addition, the tibial shell 71 has sections 75—75 which partially wrap around the posterior of the leg and the femural shell 72 has sections 76—76 which wrap partially around the anterior section of the femur. One purpose of these partial sections is to enhance the suspension characteristics of the leg; at the same time, the openings defined between sections 75—75 and between sections 76—76 contribute to the light weight and ease of application of the stabilizer 70.

The anterior sections 76—76 of the femural shell each include a stabilization or suspension tab 77 which is configured to and positioned between the patella or knee cap and the femural epicondyle located on that side of the knee. The tibial and femural shells have straps 78 and 79 respectively attached thereto for spanning their respective posterior and anterior openings to aid the suspension of the shells on the leg and thigh.

Typically the straps 78 and 79 are rigidly attached along one side, as by metal rivets, and are releasably attached on the opposite side, as by Velcro, to permit releasing the straps to fit the knee stabilizer onto the leg and to provide an adjustably snug fit of the knee stabilizer 70 onto the leg.

Referring in particular to FIG. 7, the tibial and femural shells 71 and 72 are rigidly suspended relative to one another and the knee by the band suspension system 80. This system comprises metal bands which are configured to the outline of the shells and leg. The system includes a pair of substantially vertical uprights 82—82 attached to the medial and lateral sides of the femural shell 72 and, similarly, a pair of substantially vertical uprights 83—83 attached to the medial and lateral sides of the tibial shell 71. A tibial band 84 is attached to the uprights 83—83 on opposite sides of the tibial shell 71 and spans the closed anterior section of the shell. Similarly, a femural band 85 is attached to the uprights 82—82 on opposite sides of the femural shell and spans the posterior side of the femural shell. The uprights 82 and 83 are joined proximate the knee by a conventional polycentric knee joint 86 which is designed to pivot in a curve which tracks the knee, i.e., is similar to the anatomical movement of the knee.

The knee stabilizer 70 includes several advantageous suspension features. It should be noted that the word "suspension" refers to retaining a knee brace on the knee and leg without movement, such as planing, of the brace relative to the knee. Suspension, of course, contributes to the ability of the brace to stabilize the knee and leg and many of the factors which are necessary for adequate suspension also contribute to stabilization. That is, improving suspension improves stabilization. One advantageous feature of stabilizer 70 is the custom-tailored contour of the shells 71 and 72 and band system 80. In being precisely configured to the shape of the leg and thigh, both at the anterior and posterior sides as well as the medial and lateral sides, a secure fit is provided and movement of the stabilizer relative to the leg is inhibited. A second, related aspect is that the closely configured shells of the stabilizer 70 also encompass or cover more of the perimeter of the leg and thigh than conventional braces. Third, the rigid band support system 80 comprises a unitary configuration which tracks the primary stress points (the back of the thigh, the front of the tibia, and the sides of the legs), and thereby keeps the configured shells firmly in place on the leg and contributes to excellent stability. Also, as mentioned above, the polycentric knee joints 86—86 track in a curve much the same as does the knee, which facilitates maintaining the shells in position during flexion and extension of the knee. Fifth, the knee joint 86 can be misaligned slightly. That is, (1) the joints can be rotated slightly relative to the anatomical track to create a stabilizing force at the anterior superior edges of the tibia to stabilize rotatory instabilities or (2) the knee joint 86 can be misaligned or offset relative to the anatomical knee so that the plastic material of the shell bends faster than the knee and thus maintains pressure on the knee to counter anterior cruciate instability of the knee. For example, the joint 86 can be positioned posteriorly and/or superiorly relative to the anatomical knee center to counter the inherent instability of the knee during 20°–60° of flexion, or the joint can be positioned rotationally to the knee center to counter the anterior rotatory displacements of the tibia. An example of such positioning is illustrated in FIG. 7 wherein the orthosis knee center provided at knee joint 86 is positioned above the anatomical knee center 87 so that, e.g., in flexing as shown in phantom by line 880 the orthosis flexes faster than does the knee at 88A and creates posterior pressure on the knee and leg.

Sixth, the brace incorporates a circumferential perimeter differential. That is, the distal border (lower portion) of the femural shell 72 has a smaller circumference than the adjacent underlying femural condyles. This is done to apply pressure to the anterior edges of the abductor and adductor epicondyles on the medial and lateral sides of the femural condyles. A seventh, related feature is the suspension tabs 77—77 which are discussed below. Finally, but not to exhaust the advantages, an auxiliary strap can be used to connect the superior border of the tibial shell to provide additional stabilization against inertia in unusually high stress situations.

In considering the stabilization characteristics of the knee stabilizer 70, refer initially to the front and rear depictions of FIGS. 8 and 9, as well as the side view of FIG. 7. In contrast to prior art braces, the stabilizer 70 stabilizes against medial-lateral forces very well, in part because the shells 71 and 72 circumferentially encompass more of the leg than prior art braces. The shells fully cover both the lateral and medial sides of the thigh and leg proximate the knee. Displacement side-to-side is further constrained by the closed anterior section of the tibial shell 71, the partial wraparound of the posterior section 75 of the tibial shell, the closed posterior section of the femoral shell 72 and the partial wraparound of the anterior section 76 of the femoral shell, in conjunction with the additional constraint against side-to-side displacement provided by the closed configuration of band 80, that is the posterior femoral band 85, the anterior tibial band 84 and the interconnecting uprights 82 and 83. In contrast to the three-point medial-lateral suspension of many prior art braces, the described construction of the knee stabilizer 70 provides essentially continuous support and stabilization against displacement from the lower or distal edge of the tibial shell 71 to the upper or superior edge of the femoral shell 72.

Those skilled in the art will appreciate that the above-described structural features which provide medial-lateral stability also contribute to anterior-posterior stability. The structure of the knee stabilizer 70 incorporates key pressure points which are designed to protect against anterior-posterior instability as well as medial-lateral and rotary instability. Referring to FIG. 7, five of these points are indicated generally by the arrows designated 91-95. These include three pressure points or regions which securely lock the tibia: the distal (lower) 91 and proximal (upper) 92 borders of the closed anterior tibial shell section 73, and the posterior point 93 defined by the posterior section and elastic strap 78 of the tibial shell; and two femoral pressure points: the anterior proximal (superior) femoral border 94 and the posterior distal border 95 of the closed posterior section 74 of the femoral shell. Also, due to the large amount of tendon motion in the distal posterior border of the femoral section, the inverted popiteal-shaped relief 74 is preferably set in a slight lateral tilt.

Those skilled in the art will quickly appreciate that the other structural features such as tabs 77—77 also serve important stabilization functions.

The effectiveness of this suspension and pressure system design can be illustrated by considering application of the anterior tibial force 21 shown in FIG. 2A and the external rotation anterior tibial force 21-22 shown in FIG. 2B. As indicated previously, these are frequently responsible for injury to the anterior cruciate ligament, perhaps the most frequency injury in sports. In response to an anterior tibial force 21 of sufficient magnitude, the tendency is for the lower leg 12 to move and potentially injure the anterior cruciate ligament. However, this movement transmits pressure against the closed borders 96 and 97 of the anterior section 73 of the tibial shell 71 and tends to move the tibial shell. This tendency is in turn transmitted via the band support system 80 and femur band 85 thereof to the femoral shell 72. The closed posterior section 74 and, in particular, the distal border pressure 95 transmit any displacement of the lower leg into like displacement of the thigh and thereby prevent displacement of the tibia 12 relative to the femur 11. In short, the anterior-directed tibial force 21 is transmitted as an anterior-directed femoral force to stabilize the femur and tibia and prevent relative displacement.

Considering now the rotational component 22 of the exterior force, one will recall that the tendency of prior art braces is to rotate on the leg. In the knee stabilizer 70, an additional stabilizing influence to those previously described is provided by the stabilizing pads 77—77 which provide pressure at the distal border of the anterior femural shell section 76. In response to such rotational forces (either or both anterior-lateral or anterior-medial), one of the pads 77 is constrained from movement by the opposite epicondyle, while the other pad is constrained by the patella. As a result, the anterior cruciate ligament is stabilized, along with the other knee ligaments and the entire knee. In addition, those skilled in the art will appreciate that rotational forces and rotary instability are functions of the force vectors in the frontal plane (medial-lateral forces) and the sagittal plane (anterior-posterior forces). Thus, derotation and rotary stability are aided by the features described previously which contribute to enhanced anterior-posterior stability and medial-lateral stability.

In working embodiments of the knee stabilizer 70 designed for a six foot, 180 pound male, the overall length of the stabilizer was 19.5 inches. The femural shell was polypropylene plastic three-sixteenths of an inch thick while the tibial shell was one-eighth inch thick polypropylene. The shells were lined with one-quarter inch thick medium density aliplast. The bands and uprights were both made of 2024 aluminum alloy to provide light weight and strength. The bands ranged from one-eighth by three-quarters inch to one-eighth by one and one-half inch, depending upon the patient's size and activities, while the uprights were one-eighth by three-quarters of an inch. The joints were Becker 1009B aluminum polycentric knee joints, formed by machining to provide enhanced smoothness and tracking. Silver solder can be inserted into the joint gear to limit flexion to a prescribed range. The straps 78 and 79 were gum rubber reinforced by leather at the Velcro and Dacron at the copper rivet attachment points. The resulting stabilizer weighed 24-40 ounces and provided excellent movement and mobility.

A presently preferred, four-point pressure version 70' is illustrated in FIGS. 10-12. Specifically, the stabilizer or brace 70' is a three-point pressure system with a fourth inertial control strap. In describing the four-pressure point brace 70', components which correspond to, or are modified versions of, components of the five-pressure point brace 70 illustrated in FIGS. 7-9 are identified by corresponding numbers differentiated by the prime symbol. Thus, for example, the modified tibial shell 71' of the four-point pressure brace 70' corresponds to the tibial shell 71 of the five-point pressure brace 70.

The femoral shell 72' of the four-pressure-point brace 70' includes elongated medial and lateral sections 76'—76' which extend farther up the thigh than do the corresponding components 76—76 of brace 70, FIG. 7. Anterior strap 79 is omitted. In its place is provided a typically elongated anterior plate 98 which is positioned between the elongated medial and lateral upright sections 76'—76' The anterior plate 98 typically is mounted to the femural shell 72' by a pair of straps or belts 99—99. The belts 99—99 can be single-piece continuous straps which are fastened by buckles, Velcro, etc.

In the illustrated embodiment, each belt 99 includes a strap or belt section 101 which is riveted at one end to one upright section 76' of the femural shell and mounts a buckle 102 at the loose end. A second strap or belt section 103 is attached by rivets to the other upright section 76' of the femural shell 72'. The belt section 103 also extends across, and is riveted to, the plate 98, and is of sufficient length to permit looping of its end 104 through the buckle 102 to provide an adjustable, loop-back fastening or closing of the belt 99.

Typically, each belt 99 is adjustably fastened by, for example, mating lengths of Velcro fastening material 105 which are attached to the outer-facing surface of the inner portion of the belt section 103 and to the inner-facing surface of the overlapping end 104 of the belt section 103. The belts 99 can be elastic material, but, preferably, are formed of inelastic material such as Dacron. An inelastic or fixed system provides better anterior pressure on the quadricep muscle and also transfers force better than an elastic system. As a result, the femural pressure point at 94' is improved. The other, second femural pressure point is provided by the posterior border 74' of the femural shell 72' and the associated posterior femural band 85' corresponding to the pressure point 74 of the five-pressure-point shell 70. Quite obviously, an inelastic, fixed belt or strap system can be implemented in the five-pressure-point system 70 as well as in the present four-pressure-point system 70'

Referring further to FIGS. 10-12, the tibial shell 71' of the four-pressure-point brace is shorter, smaller and therefore of lighter weight than the tibial shell 71, FIGS. 7-9. The tibial shell 71' provides two pressure points (the third and fourth system pressure points), rather than the three points of the alternative five-pressure-point embodiment 70. The narrower elastic band or strap 78' which spans the posterior opening of the tibial shell 71' provides the third pressure point of the system. The fourth pressure point of the brace is provided at the superior anterior band 96' of the tibial shell 71'. To decrease weight, the lower anterior band 97 of the five-pressure-point brace 70 (FIG. 7) is omitted and, as a consequence, the lower ends of the medial and lateral upright shell sections 73'—73' terminate in the open configuration which is shown most clearly in FIGS. 8 and 9. In addition, the anterior tibial band 84' of the band pressure system is moved to the superior band or border 96' to enhance the rigidity and support at the fourth pressure point. Suspension of the tibial shell 71' on the leg is further enhanced by a circumferential strap or belt 106 which spans the circumference of the leg. While various constructions and means of attaching the belt 106 are possible and in fact, while it need not be attached to the tibial shell 71', the belt 106 typically is attached to the tibial shell 71' by rivets and is closed by using lengths of Velcro 107 which are attached to the outer-facing surface of the belt and to the inner-facing surface of the overlapping end of the belt.

In summary, in the four-pressure-point brace 70', the lower anterior band 97 of the tibial shell is eliminated and the metal strut 84 of the band system is moved vertically, as shown at 84', and incorporated into the upper anterior tibial band 96'. The posterior elastic band 78' of the tibial shell is more narrow than band 78. Also, the anterior elastic band 79 of the femural shell has been replaced by an inelastic fixed-strap system which incorporates belt(s) 99 and anterior pressure plate 98.

Referring specifically to FIG. 10, in addition to lighter weight, this alternative brace construction 70' provides an improved pressure system. As mentioned, the four-point pressure system is effectively a three-point pressure system with a fourth, inertial control strap, the posterior tibial strap 78'. The four pressure points are first, the posterior femural point 95'; second, the anterior femural point 94'; third, the above-mentioned posterior tibial point 93'; and fourth, the anterior tibial point 92'. The objective of the system is to apply force at anterior tibial point 96', using the brace and its band system as a lever system and the posterior femural point 95' as the fulcrum. Pressure is applied at the anterior femural point 94' by the adjustable strap system 99. That is, when pressure is increased at point 94' by tightening the belts 99, the femural section of the band system is pulled anteriorly. This force is transmitted through the fulcrum at 95' and therefore pivots the tibial section of the band system, along with the knee joints and the band section 96', posteriorly. As a result, tightening at one point, using belts 99 securely suspends the knee stabilizer 70' on the leg and provides an optimum combination of light weight and anterior-posterior, medial-lateral and rotary stability.

In a working embodiment of the knee stabilizer 70', designed for a six foot, 180 pound male, the overall length of the stabilizer was 19.5 inches. Both the femural shell and the tibial shell were one-eighth inch thick polypropylene plastic. The shells were lined with one-eighth inch thick medium density aliplast. The bands and uprights were both made of 2024 aluminum alloy to provide light weight and strength. The bands measured one-eighth inch by three-quarters of an inch, while the uprights were one-half inch by one-eighth inch. The pivotal joints of the band system were Becker 1009C aluminum polycentric knee joints, formed by machining to provide enhanced smoothness and tracking. The posterior tibial strap was gum rubber reinforced by leather at the Velcro and by Dacron at the Speedy rivet attachment points. The anterior femural pressure plate was also formed of one-eighth inch thick polypropylene and the Dacron attachment straps were riveted to the plate and to the femural shell by Speedy rivets. The resulting knee stabilizer weighed between 14 and 24 ounces, depending upon the size and girth of the patient and the patient's activities, and provided excellent movement, mobility and stability.

The combination of light weight, freedom of movement and stabilization provided by the above-described four-pressure-point and five-pressure-point embodiments of the knee stabilizer or brace 70 make it suitable for both preventive and remedial use. For light weight and preventive use, the thickness of the materials can be reduced, the shells can be drilled or extensive use made of apertures or other openings and the size of the solid anterior and posterior sections reduced. To give only one illustration f the value of such preventive use, in the National Football League, approximately 50 percent of injuries involve the knee. This means during the 1983 season perhaps five to seven of the fourteen linemen on each team will have suffered disabling knee injuries. This figure could be substantially reduced by the preventive use of an effective knee stabilizer.

For remedial use to protect against further aggravation of existing injuries and instabilities, the thickness and other dimensions can be tailored as required by the orthotics specialists to fit individual needs. In addition, in applications requiring very great strength and stability, albeit at the sacrifice of slightly greater weight, a material such as stainless steel can be used for the band system. One potential use which might require this substitution is mountain climbing, where safety considerations are paramount and repair or replacement may not be available.

Having thus described the knee stabilizer which embodies the principles of my invention, and specific examples of its use, the invention which I claim is:

1. A knee stabilizer, comprising
   an elongated relatively rigid anterior tibial shell substantially conformed to the leg of a wearer including the region adjacent the knee and defining a posterior opening;
   an elongated relatively rigid posterior femural shell substantially conformed to the thigh of the wearer including the region adjacent the knee and defining an anterior opening;
   the femural shell forming a first posterior pressure section, and further comprising relatively rigid strap means spanning the anterior opening at the superior border thereof and including a rigid anterior femural plate for providing a second pressure section above the first pressure section;
   a substantially closed rigid band system comprising: a pair of uprights extending one on the lateral side of the knee and one on the medial side of the knee and rigidly connecting the tibial and femural shells, each upright having a pivotal construction proximate the knee for substantially tracking flexion of the knee; a femural band section attached to the uprights on opposite sides of the femural shell and spanning the posterior side of that shell proximate the first pressure section; and a tibial band section attached to the uprights on opposite sides of the tibial shell and spanning the anterior side of that shell; and
   the tibial shell forming a third superior anterior tibial pressure section adjacent the knee and further including strap means spanning the posterior tibial shell opening for providing a fourth pressure section proximate the distal border of said shell below the third pressure section; whereby
   the four pressure sections provide a stable, four-point pressure system for restraining rotation and displacement of the knee.

2. A knee stabilizer, comprising
   a relatively rigid anterior tibial shell conforming to the shape of the leg of a wearer and defining a posterior opening, the tibial shell including strap means at the superior region thereof for enclosing the leg;
   a relatively rigid posterior femural shell substantially conforming to the shape of the thigh proximate the knee and defining an anterior opening; the femural shell forming a first, posterior femural pressure application section, and also comprising lateral and medial sections extending to the anterior side of the thigh and defining an anterior opening, and further comprising a pair of tabs at the superior border of the lateral and medial sections on opposite sides of the patella between the patella and the femural epicondyles, and strap means spanning the anterior opening;
   an anterior femural plate attached to the femural strap means for defining a second, superior anterior femural pressure section spaced upwardly from the first pressure section;
   a substantially closed rigid band system comprising: a pair of uprights extending one on the lateral side of the knee and one on the medial side of the knee and rigidly connecting the tibial and femural shells, each upright having a pivotal construction proximate the knee for substantially tracking flexion of the knee; a femural band section attached to the uprights on opposite sides of the femural shell and spanning the posterior side of that shell proximate the first pressure region; and a tibial band section attached to the uprights on opposite sides of the tibial shell and spanning the superior anterior side of that shell; and
   the tibial shell having a superior anterior region thereof forming a third pressure section proximate the tibial band section; and further, mounting strap means which span the posterior tibial shell opening for providing a fourth, lower pressure section; whereby
   the superior tibial shell strap means provides tibial inertial control and cooperatively functions with the pair of tabs for enhancing the suspension of the stabilizer on the wearer, and the four-point pressure system provides anterior-posterior, medial-lateral and rotary stability to the knee.

* * * * *